United States Patent
Norman et al.

(10) Patent No.: US 6,294,510 B1
(45) Date of Patent: Sep. 25, 2001

(54) HALOGEN-RELEASING COMPOSITION FOR LAVATORY CLEANSING

(75) Inventors: Russell Norman; Brain Murie Wilson, both of Diss; John Marshall, Sunningdale, all of (GB)

(73) Assignee: Jeyes Group Limited (GB)

( * ) Notice: Subject to any disclaimer, the term of this patent is extended or adjusted under 35 U.S.C. 154(b) by 0 days.

(21) Appl. No.: 08/930,391

(22) PCT Filed: Mar. 27, 1996

(86) PCT No.: PCT/GB96/00759

§ 371 Date: Jan. 8, 1998

§ 102(e) Date: Jan. 8, 1998

(87) PCT Pub. No.: WO96/30491

PCT Pub. Date: Oct. 3, 1996

(30) Foreign Application Priority Data

Mar. 27, 1995 (GB) .................................................. 9506172

(51) Int. Cl.⁷ ................................ C11D 1/14; C11D 1/37; C11D 3/395
(52) U.S. Cl. ........................ 510/191; 510/193; 510/238; 510/379; 510/381; 510/446; 510/447; 252/186.34; 252/186.35; 252/187.1; 252/187.34
(58) Field of Search ..................................... 510/191, 193, 510/238, 379, 446, 447, 381; 252/186.34, 186.35, 187.1, 187.2, 187.34

(56) References Cited

U.S. PATENT DOCUMENTS

| 4,269,723 | * | 5/1981 | Barford et al. | 510/192 |
|---|---|---|---|---|
| 4,560,766 | * | 12/1985 | Girard et al. | 548/311 |
| 5,178,787 | * | 1/1993 | Hung et al. | 510/192 |
| 5,395,546 | * | 3/1995 | Hung et al. | 510/192 |
| 5,578,559 | * | 11/1996 | Dolan et al. | 510/192 |
| 5,610,126 | * | 3/1997 | Barford et al. | 510/191 |
| 5,630,883 | * | 5/1997 | Steer et al. | 134/122.13 |
| 5,750,061 | * | 5/1998 | Farina et al. | 264/117 |
| 5,756,440 | * | 5/1998 | Watanabe et al. | 510/191 |
| 5,759,974 | * | 6/1998 | Menke et al. | 510/191 |
| 5,763,376 | * | 6/1998 | Ward et al. | 510/191 |

FOREIGN PATENT DOCUMENTS

| 0 055 100 | 6/1982 | (EP) . |
|---|---|---|
| 0 101 402 | 2/1984 | (EP) . |
| 0 206 725 | 12/1986 | (EP) . |
| 0 462 643 A1 | 12/1991 | (EP) . |
| 0 526 437 A1 | 2/1993 | (EP) . |
| 2 273 106 A | 6/1994 | (GB) . |
| WO 92/18605 | 10/1992 | (WO) . |
| WO 94/12612 | 6/1994 | (WO) . |

OTHER PUBLICATIONS

McCutcheon's Emulsifier's and Detergents, International Edition, The Manufacturing Confectioner Publishing Co., 1985, p. 93. TP990D4, 1985 No month available.*

* cited by examiner

Primary Examiner—Gregory DelCotto
(74) Attorney, Agent, or Firm—Harness, Dickey & Pierce, P.L.C.

(57) ABSTRACT

A solid lavatory cleansing composition comprises: (i) a halogen-release agent containing at least 30 mole % of active halogen; (ii) a substantially non-oxidizable, substantially anhydrous surfactant component; and (iii) a substantially non-oxidizable solubility retardant agent.

6 Claims, No Drawings

HALOGEN-RELEASING COMPOSITION FOR LAVATORY CLEANSING

This invention is concerned with improvements in and relating to lavatory cleansing.

In particular, the present invention is concerned with solid lavatory cleansing compositions intended to be brought into contact with the flush water of a lavatory or urinal whereby a part of the composition is dissolved in the flush water to release active ingredients thereto for cleaning the lavatory or urinal. The compositions are immersed in the water cistern of a lavatory or urinal, either as free-standing blocks or may be placed or contained in a dispensing device, to be sited in a lavatory cistern. The invention is also concerned with lavatory cleansing compositions for intermittent contact with the flush water of a lavatory or urinal, e.g., a so-called "rim block" for placing in a container to be held under the rim of a lavatory, or else on top of a tank or cistern wash hand basin such as is common in Japan.

A desirable component of such blocks is a halogen release agent, that is a compound which on contact with water releases hypohalous acid and/or hypohalite ions to the water, since these are powerful sanitising and cleansing agents.

However, such components are highly reactive and hence may be difficult or even dangerous to incorporate in lavatory cleansing blocks. This is especially the case with the more highly reactive halogen release agents such as the halogenated hydantoins, halogenated glycolurils or trichloroisocyanuric acid. These more highly active halogen-release components may be characterised by their halogen content, typically having an active halogen content of 30 mole %, or higher.

In particular, WO 92/18605 discloses a solid lavatory cleansing block comprising one or more anionic surfactants, a halogen release agent component and a solubility control agent. However, this does not teach how to form a stable block based on a halogen release component having an active halogen content of at least 30 mole %. Examples of blocks which contain such high halogen levels (i.e. DCDMH and BCDMH) are described in EP-A-0 206 725. However, in practice it is not possible to achieve a sufficient degree of stability for commercial use with these particular formulations.

Two-part lavatory blocks in which the bleach and bleach sensitive components are kept in separate parts are disclosed in EP-A-055 100 and EP-A-101 402. DCDMH is recited as an optional bleach component in both documents.

The use of certain solubility retardants in combination with bleaches (which are not those containing at least 30 mole % of active halogen) are disclosed in WO 92/18605 and GB-A-2 273 106.

It has now been found, in accordance with the present invention, that halogen-release agents may readily be incorporated in certain lavatory cleansing compositions, as hereinafter defined.

According to the invention, therefore, there is provided a solid lavatory cleansing composition comprising:

(i) a halogen-release agent, containing at least 30 mole % active halogen;

(ii) a substantially anhydrous surfactant component; and (iii) a solubility retardant agent;

wherein components (ii) and (iii) are substantially non-oxidisable.

Thus, a particular non-limiting embodiment of the invention provides a solid lavatory cleansing block formed of a composition comprising (A) from 1 to 80%, preferably from 20 to 60%, by weight of the surface active component comprising one or more substantially anhydrous, substantially non-oxidizable anionic surface active agents; (B) from 1 to 90%, preferably from 1 to 50%, e.g. 1 to 30% by weight of halogen-release agent; and (C) from 1 to 50%, preferably from 1 to 30%, by weight of a substantially non-oxidizable solubility control agent (as hereinafter defined).

Examples of highly active halogen-release agents which may be employed alone or in combination in this system include:

N,N'-dichloro-dimethyl-hydantoin (DCDMH-av. halogen 34 mole %), N-bromo-N'-chloro-dimethyl-hydantoin (BCDMH-av. halogen 48 mole %) and N,N'-dibromo-dimethyl-hydantoin (NBDMH-av. halogen 56 mole %), as well as other halogenated alkylated hydantoins, and trichloroisocyanuric acid (TCAA, av halogen 46 mole %). N,N,N,N-tetraglycoluril (av. halogen 50 mole %).

Suitable surface active agents for use in the composition of the invention are anionic surface active agents, especially alkali metal, typically sodium, alkyl sulphates (e.g. lauryl sulphate), primary and secondary alkane sulphonates or sarcosinates or mixtures thereof, provided that these are in substantially non-oxidizable and substantially anhydrous form. In the context, "substantially anhydrous" means that the water content as expressed as the total of free and banded water in the surfactant is preferably less than 2% by weight of the surfactant sample, more preferably less than 1% by weight.

The solubility control agent should also be substantially non-oxidizable. It is selected from one or more such materials. Provided that this criterion is met, such agents may be virtually wholly insoluble in water or if, as discussed below a nonionic surface active agent, have a low HLB, e.g. 5 or less. Such agents being substantially non-oxidizable are substantially resistance to attack by the halogen release component, both in the composition and in aqueous solutions produced by dissolution of the composition in use. It is a matter of simple experiment to determine whether any candidate is so resistant. Generally, the solubility control agent should be a saturated organic material or a highly chlorinated organic material. Examples of solubility agents which may be employed include polyethylene waxes; saturated tertiary alcohols; paradichlorobenzene; and difficulty hydrolysable esters.

Provided that they meet the criterion of being substantially non-oxidizable, such solubility control agents may also be chosen from non-oxidizable organic liquids. A wide variety of these may be employed, such as mineral oils, liquid hydrocarbons (e.g. liquid alkanes), chlorinated hydrocarbons, silicone oils, liquid ketones (e.g. 2-decanone), liquid tertiary alcohols (e.g. 2-methyl-hexan-2-ol), and liquid esters e.g. simple esters such as methyl decanoate, and more complex esters such as glycerol, propylene glycol, triethylene glycol esters of $C_8$–$C_{10}$ fatty acids and/or succinic acid. Examples of such complex esters are those sold under the trade name MIGLYOL 812, MIGLYOL 829, MIGLYOL 840, PLASTHALL 4141, CRODAMOL GTCC, CRODAMOL PC and RADIA 7108.

Particularly preferred examples of such solubility control agents include solid esters; waxes; saturated fatty acid esters; mineral oils; and polysiloxanes. It has been found that the use of a mixture of non-oxidizable solubility control agents may often prove useful. Thus a mixture of an essentially hydrocarbon material, such as paraffin wax and/or a mineral oil, with an ester of a fatty acid such as isononyl stearate or triethylene glycol, caprate/caprylate, may be employed. Further, it is sometimes useful to employ, in admixture, a combination of both a solid and a liquid hydrocarbon material. Other substantially non-oxidizable solubility control agents include glycolurils and inorganic compounds such as aluminium hydroxide.

As will be appreciated, any other ingredient present in the compositions of the invention (whether surfactant-containing or not) should be resistant to attack by the halogen release agent. Most perfumes which are commonly employed in lavatory cleansing blocks are also subject to attack by halogen-release agent although some odiferous materials may be adequately resistant (and additionally serve as solubility control agents). Adequately resistant examples of these include substituted quinolines, cedryl methyl ether and cineole. Many of these perfumes are suitable also to fulfill the role of the solubility control agent as well as to function as processing aids, e.g. in an extrusion process. Particular examples of perfumes include CITRUS 4022 ex IFF, PINE 2363 ex IFF, FANTASY 2366 ex IFF, ARTIC FRESH 2662 ex IFF, and ORIENTAL FRUITS F540096 ex QUEST, all these names being Trade Marks.

Fillers, typically mineral fillers, may be present in the blocks and are suitably present in amounts of from 1 to 75% by weight, preferably 1 to 50% by weight, e.g. 1 to 30% by weight. The filler is often required to increase the density, life or integrity of the block and suitable examples are salts such as calcium sulphate and sodium sulphate, as well as clays such as laponite.

Lavatory cleansing blocks commonly contain a germicide or preservative but this is not generally necessary in the case of the blocks of the invention since they already contain a powerful germicide(s), namely the halogen-release agent.

Some insoluble pigments are resistant to halogen release agents and may be incorporated in the blocks of the invention to impart a coloration.

Suitable examples include inorganic pigments of mixed-phase types, consisting exclusively of metal oxides such as Co/Al oxide (blue) and Co/Ti/Ni/Zn oxides (Green). These can be conveniently incorporated in the blocks of the invention by dispersing in the powder mixture.

Solid blocks may suitably be formed by a compression process, especially an extrusion or tabletting process. For extrusion, this comprises the steps of forming a mixture of the components of the composition, extruding this mixture into rod or bar form and then cutting the extruded rod or bar into appropriately sized pieces or blocks.

Alternatively, blocks may be prepared by a melting and casting process, e.g. one in which fusible components of the block are fuse melted, the non-fusible components adhere to the melt, and the resultant mixture cast into moulds.

When an extrusion process is employed the mixture to be extruded should contain up to 25% by weight, of a liquid component or a solid component which is liquefied under extrusion conditions to act as a processing aid. Suitable such liquids include hydrocarbons (e.g. liquid alkanes), polysiloxanes, chlorinated hydrocarbons, silicone oils, liquid ketones (e.g. 2-decanone), liquid tertiary alcohols (e.g. 2-methyl-hexan-2-ol), and liquid esters e.g. simple esters such as methyl decanoate, and more complex esters such as glycerol, propylene glycol, triethylene glycol esters of $C_8$–$C_{10}$ fatty acids and/or succinic acid. Examples of such complex esters are those sold under the trade names Miglyol 812, Miglyol 829, Miglyol 840, Plasthall 4141, Crodamol GTCC, Crodamol PC and Radia 7108. These liquid components can also serve as solubility control agents. Suitable liquefiable solid components include solid esters such as cetyl palmitate and these also can serve as solubility control agents In order that the invention may be well understood the following examples are given by way of illustration only. All amounts are expressed as percentages by weight unless explicity recited to the contrary. Typical block weights are from 25 g to 150 g e.g. from 30 to 120 g.

Blocks having a weight of 50 g were prepared by melting and casting the following composition:

| Constituents | Example 1 % w/w |
|---|---|
| DBDMH | 20 |
| Sodium Lauryl Sulphate | 25 |
| Laponite | 15 |
| Paraffin Wax | 10 |
| Mineral Oil | 15 |
| Isononyl Stearate | 15 |

Where:
DBDMH is dibromodimethylhydantoin in powder form ex Peboc.
Laponite is a smectite type clay.
The following were prepared by an extrusion process:

| | Example | | | | | | |
|---|---|---|---|---|---|---|---|
| Constituent | 2 | 3 | 4 | 5 % w/w | 6 | 7 | 8 |
| Hostapur SAS93 (TM) (2.0% w/w MgO) | 58.80 | — | n/a | — | — | — | — |
| Hostapur SAS93 (TM) (0.5% w/w MgO) | — | 50.0 | — | — | — | — | — |
| Hostapur SAS93 (TM) (1.0% w/w CaSO$_4$) | — | — | — | — | — | 50. | — |
| Hostapur SAS93 (TM) (5.0% w/w MgO) | — | — | 41.0 | 40.9 | 40.9 | — | 54.0 |
| Calcium Sulphate | 13.7 | 21.0 | 18.0 | 18 | 18 | 23. | 25.0 |
| Plasthall 4141 (TM) | 4.90 | 3.0 | 7.0 | 7.0 | 7.0 | — | — |
| Crodamol MM (TM) | 5.90 | 9.0 | — | — | — | 7.0 | — |
| Halogen G (TM) | 16.70 | 17.0 | 17.0 | — | — | 15. | 15.0 |
| Citrus 4022 (TM) | — | — | — | — | — | 5.0 | 6.0 |
| Cetyl Palmitate | — | — | 17.0 | 17.0 | 17.0 | — | — |
| Sicopal Blue K6310 (TM) | — | — | — | 0.1 | — | — | — |
| Sicopal Green K9710 (TM) | — | — | — | — | 0.1 | — | — |
| Dantobrom RW (TM) | — | — | — | 17.0 | — | — | — |
| Biolab Bromicide (TM) | — | — | — | — | 17.0 | — | — |
| Rimstick/Ontank Block (50 g) | Yes | Yes | Yes | Yes | Yes | Yes | Yes |
| Intank block (60 g) | No | No | Yes | Yes | Yes | Yes | Yes |

TM = Trade Mark

Where:
   Hostapur SAS 93 is a 93% active secondary alkane sulphonate in powder form, incorporating inorganic salts as declared (balance is sodium sulphate) ex Hoechst.
   Halogen G is a 92% active BCDMH in granular form, incorporating boric acid and sodium chloride as declared ex Rohm & Haas.
   Dantobrom RW is a combination of BCDMH, DCDMH and DCEMH in powder form ex Lonza Inc.
   Plasthall 4141 is triethylene glycol caprate caprylate in liquid form ex CP Hall.
   Biolab Bromicide is a 100% active BCDMH in powder form ex Great Lakes Chemical (Europe) Ltd.
   Crodamol MM is myristyl myristate in solid form ex Croda Chemicals.

Citrus 4022 is a suitable fragrance ex IFF.
Sicopal Blue K6310 is a Co/Al oxide pigment in powder form ex BASF.
Sicopal Green K9710 is a Co/Ti/Ni/Zn oxide pigment in powder form ex BASF.

| Constituents | 9 % w/w | 10 % w/w |
|---|---|---|
| Hostapur SAS93 (TM) (5% w/w MgO) | 39 | — |
| Cetyl Palmitate | 17.0 | — |
| Calcium Sulphate | 18.0 | 18.0 |
| TCCA | 17.0 | — |
| Plasthall 4141 (TM) | 9.0 | 5.0 |
| Crodamol SS (TM) | — | 20.0 |
| Hamposyl L95 (TM) | — | 35.0 |
| Halogen G (TM) | — | 17.0 |
| Citrus 4022 (TM) | — | 5.0 |
| Rimstick/Ontank block (50 g) | Yes | Yes |
| Intank | Yes | Yes |

Where:
TCCA is 100% active trichloroisocanuric acid in powder form ex Chlorchem.
Crodamol SS is a blend of synthetic fatty acid esters in powder form ex Croda Chemicals.
Hamposyl L95 is 95% active sodium lauryl sarcosinate in powder form ex Hampshire Chemicals.

What is claimed is:

1. A solid lavatory cleansing block composition comprising:
   (i) from 1% to 90% by weight of a halogen-release agent containing at least 30 mole % of active halogen;
   (ii) from 1% to 80% by weight of a substantially anhydrous anionic surfactant component selected from the group consisting of alkyl sulphates, primary and secondary alkane sulphonates and sarcosinates, salts thereof, and mixtures thereof; and
   (iii) from 1% to 50% by weight of a solubility control agent;
   wherein components (ii) and (iii) are substantially non-oxidizable.

2. The composition according to claim 1, wherein the halogen release agent comprises an halogenated alkylated hydantoin.

3. The composition according to claim 2, wherein the halogenated alkylated hydantoin comprises one or more agents selected from the group consisting of N,N'-dichloro-dimethyl-hydantoin, N-bromo-N'-chloro-dimethyl-hydantoin, and N,N'-dibromo-dimethyl-hydantoin.

4. The composition according to claim 1, wherein the halogen release agent comprises trichloroisocyanuric acid.

5. The composition according to claim 1, wherein the halogen release agent comprises N,N,N,N-tetraglycoluril.

6. The composition according to claim 1, further comprising from 1 to 75% by weight of a mineral filler.

* * * * *